United States Patent [19]

Guena et al.

[11] Patent Number: 5,417,651
[45] Date of Patent: May 23, 1995

[54] PUNCTUM PLUG AND MONOCANALICULAR PROBE FOR LACRIMAL PATHOLOGY

[76] Inventors: Nicolas Guena, 124, avenue Carnot, F-92150 Suresnes; Sylvain Auvert, 1, avenue Pierre Grenier, F-92100 Boulogne Billancourt, both of France

[21] Appl. No.: 87,623

[22] Filed: Jul. 1, 1993

[51] Int. Cl.⁶ ............................................. A61M 5/00
[52] U.S. Cl. .............................. 604/8; 604/294; 606/107; 606/198
[58] Field of Search .............. 604/8, 294; 606/107, 606/191, 198, 199

[56] References Cited

U.S. PATENT DOCUMENTS

| | | |
|---|---|---|
| 3,949,750 | 4/1976 | Freeman . |
| 4,574,000 | 3/1986 | Hunter ................................. 604/8 |
| 4,816,016 | 3/1989 | Schulte et al. ...................... 604/8 |
| 4,840,190 | 6/1989 | Sasaki .................................. 604/8 |
| 5,163,959 | 11/1992 | Herrick ............................ 604/294 |
| 5,178,604 | 1/1993 | Baerveldt et al. ................. 604/8 |
| 5,192,301 | 3/1993 | Kamiya et al. ................. 606/198 |
| 5,283,063 | 2/1994 | Freeman ........................ 604/294 |

FOREIGN PATENT DOCUMENTS 0181165 5/1986 European Pat. Off. .
2632531 12/1989 France .

*Primary Examiner*—Paul Prebilic
*Attorney, Agent, or Firm*—Eckert Seamans Cherin & Mellott

[57] ABSTRACT

A punctum plug and probe for lacrimal pathology includes the plug having a flange, a neck and a bulb portion, wherein the flange is inclined at an angle of approximately 130° with respect to the symmetry axis, the foot portion being radially flexible from its resting position towards the symmetry axis, and the plug constitutes a head for the probe.

4 Claims, 2 Drawing Sheets

PUNCTUM PLUG AND MONOCANALICULAR PROBE FOR LACRIMAL PATHOLOGY

The present invention relates to a punctum plug and a monocanalicular probe for lacrimal pathology using such a plug.

BACKGROUND OF THE INVENTION

Method for treating external human eye diseases due to a deficiency of tears are known which consist of using punctum plugs and implants to treat keratoconjonctivis sicca, referred to in common language as "dry eye", due to the insufficient production of tears or to an excessive drainage of the lacrimal liquid.

This disease is relatively frequent, particularly among the elderly. With age, the eye produces less tears (about 0.6 times less at the age of 65 than at the age of 18). The tears are generated permanently by small glands and temporarily by the large lacrimal gland flow over the eye and drain through small openings called puncta in the lids of the eyes corresponding with canaliculi which direct the tears towards the nose.

Some devices have already been proposed to be placed in the lacrimal system to diagnose and treat various conditions. One of these devices is known as punctum plug and is described by Jerry M. FREEMAN, MD., in US. Pat. No. 3,949,750. This plug is designed to completely close the punctum opening and comprises a slightly larger portion projecting in the vertical portion of the canaliculus that prevents the plug from extruding and a larger smooth head at the upper part that prevents the plug from passing down into the canaliculus.

The head is dome shaped to allow it to rest in the lacrimal pool and against the conjunctiva and cornea with little irritation. This plug, however, is prone to being pulled out by the plug wearer.

On the other hand, it is also known that a "PYREX" (registered Trademark) was designed by Dr. Lester JONES for placement in the canaliculus to maintain a pathway from the eye to the nose.

Another implant for treating external human eye conditions due to a deficiency of tears is disclosed in the European Patent No. 0,181,165 to HERRICK. A blockage is obtained in placing an implant within the horizontal portion of at least one of the canaliculi of the patient's eye.

Another known disease arises from the fact that one of the two canaliculi is stenosed and in this case the tears drain off on the patient's check in lieu of flowing through the tear ducts and out the nose. This condition becomes rapidly unbearable to the patient, the lacrimal production being permanent.

The current method to remedy this condition consists of passing a silicone tubing in the two canaliculi, upper and lower respectively, and tying the two ends of the silicone tubing in a knot inside the nose. In this case, however, the tubing appears in the palpebral opening (as a loop between the two punctae) and poses a risk of a hazardous extraction. Furthermore, only one intubation may be sufficient as it is rare that the two canaliculi are stenosed at the same time.

SUMMARY OF THE PRESENT INVENTION

One object of the invention is to propose a punctum plug which can be anchored in the punctum.

Another object of the invention is a monocanalicular probe which can be strongly secured in the canaliculus, without the need of tying any knot. This probe has been designed and manufactured to re-open a stenosed canaliculus or a lacerated one.

The invention relates to a monocanalicular probe for lacrimal pathology comprising a duct plug having a symmetry axis and including a flange, a neck and a bulb, wherein a tip extends laterally from the bulb in a direction about perpendicular to the symmetry axis of the plug, a flexible tube being adhered to said tip, said tube being ended by a mandrel.

Therefore, according to the invention the probe matches with the physiology of the canaliculus which comprises a sensibly vertical part corresponding with a sensibly horizontal part.

In the known technique of the punctum plugs, the top portion or "flange" of the plug (which may be constituted by a disk) is generally perpendicular to the axis of the plug. As a result, the edge of the flange may come into contact with the cornea when the eye is in certain positions. This contact leads to painful irritation. In some cases, the top end is hemispherical. However that leads to thicknesses which are excessive.

According to one feature of the invention, the duct plug has a flange inclined at an angle of approximately 130° in relationship with the symmetry axis. In this way, the contact between the plug and the cornea is a smooth one and does not produce any irritation.

According to the invention, the punctum plug includes a foot portion which is radially flexible. This facilitates the insertion inside the punctum because during the insertion, the flexible foot portion is folded from its rest position towards the symmetry axis upon contact with the punctum wall, while, after insertion, the foot extends radially and comes in abutment with the lower surface of the punctum so as to realise an effective anchorage.

The foregoing and other objectives, features and advantages will be more readily understood upon consideration of the following detailed description of the invention, taken in conjunction with the accompanying drawings.

DETAILED DESCRIPTION OF THE INVENTION

Figure 1:
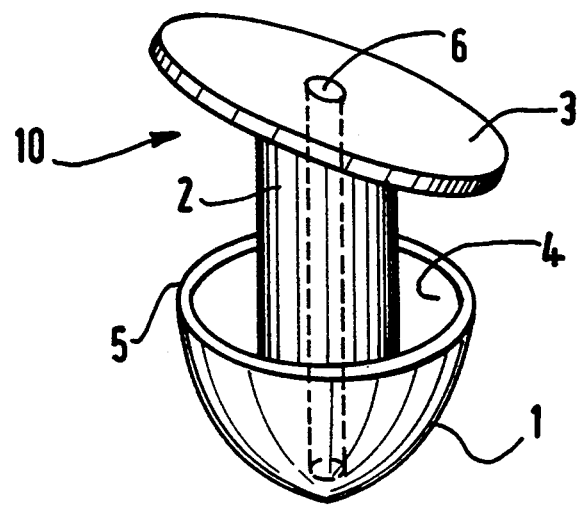
FIG. 1, is a representation of a punctum plug according to the invention.

On FIG. 1 is shown a punctum plug consisting of a foot portion or bulb 1, a neck 2 and a flange 3. The flange 3 is tilted relative to the axis of symmetry X of the plug. This tilting of the flange allows to have a full contact between the cornea and the flange thereby avoiding irritation. In conventional manner, the plug includes a blind hole 6 for positioning purposes passing through the flange 3 and the neck 2. The foot portion 1 presents the shape of an umbrella 4, ended by an edge 5, the cavity of which surrounds the neck 2 on a portion of its length. This shape gives more flexibility to insert the plug and, after expansion of the skirt 4, the plug is securely maintained inside the punctum without any risk of expulsion through an anchorage effect due to the radial flexibility of the umbrella.

Figure 2:
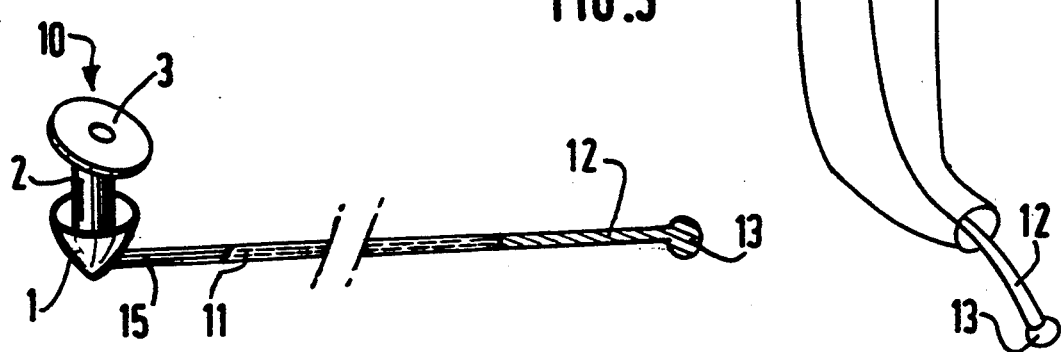
FIG. 2, is a probe according to the invention.

As shown on FIG. 2, the plug 10 can constitute the head of a probe for intubation of lacrimal ducts. From the head 10 projects a tube 11 made of silicone said tube being ended by a mandrel 12. This mandrel is preferably metallic and protected by a cover of plastic foam 13. The tube 11 is mounted on a peg 15 which protrudes from the bulb 4. The peg 15 is approximately perpendicular to the axis X of the plug to enter easily the horizontal part of the canaliculus. The tube 11 is adhered or otherwise fixed on the peg 15 by one of its ends.

Figure 3:
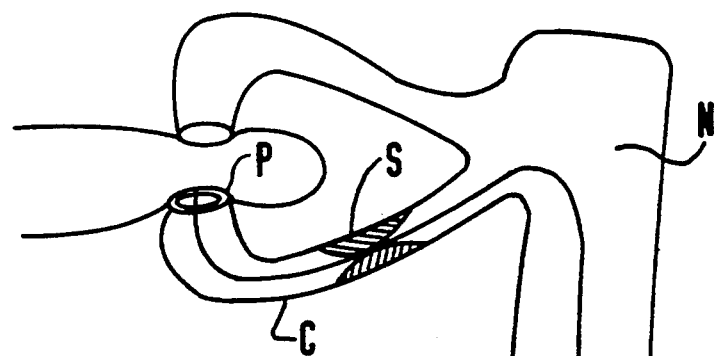
FIG. 3 is a schematic representation of a human anatomy of the excretory system with a stenosed canaliculus.

FIG. 3 represents the lacrimal system of a human being, the lower canaliculus C being stenosed at S point. A monocanalicular probe according to the invention is inserted in the lower canaliculus and runs from the punctum P towards the lower part of the nose after having traversed the stenosed zone S.

Figure 4:
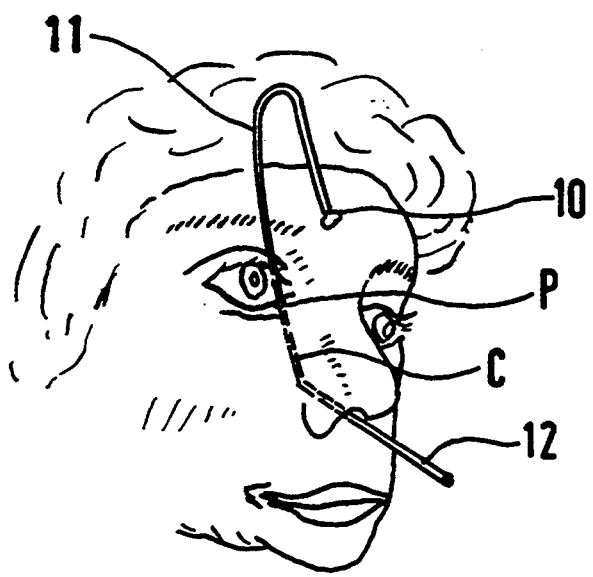
FIG. 4 is a view of the implantation of a probe according to the invention.
Figure 5:
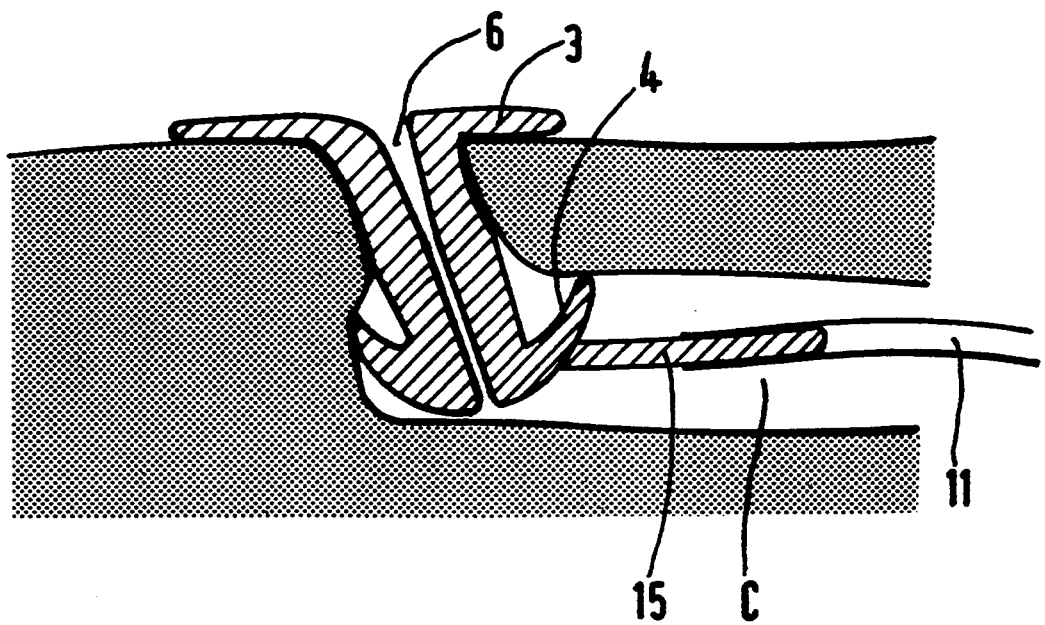
FIG. 5, is an enlarged view of the head of the probe showing how the probe can be securely fixed inside the punctum.

As it appears on FIG. 4, the mandrel 12 is first inserted inside the punctum P and through the canaliculus C, the metallic mandrel transverses the stenosed zone S (see FIG. 3). Next, the mandrel is pulled out through the nasal cavity until the mandrel can be pull out. The probe follows the path of the lacrymal duct and can be deflected to draw it out of the nasal cavity. At the end of this movement, the plug 10 passes through the punctum and is retained by the flange 3 and blocked by radial extension of the foot 1 as shown on FIG. 5.

The terms and expressions which have been employed are used as terms of description and not of limitation and the scope of the invention is limited only by the appending claims.

What is claimed is

1. A monocanalicular probe for a lacrimal pathology comprising a duct plug having a symmetry axis and including a flange on one end of said plug, a bulb on another end of said plug, and a neck extending between the flange and the bulb, wherein the flange is inclined at an angle of approximately 130° in relationship with the symmetry axis, the bulb being radially flexible from its resting position toward the symmetry axis, wherein a peg extends laterally from the bulb in a direction approximately perpendicular to the symmetry axis of the plug, a flexible tube being adhered to said peg, said tube having a mandrel on an end thereof.

2. The monocanalicular probe of claim 1, wherein the bulb includes an umbrella-shaped skirt for facilitating insertion of the plug into a punctum.

3. The monocanalicular probe of claim 2, wherein the flange is disk-shaped.

4. The monocanalicular probe of claim 2, wherein the tube is fabricated of silicon and the mandrel comprises a metallic member and a plastic foam cover.

* * * * *